US012797770B2

(12) United States Patent
Lin et al.

(10) Patent No.: US 12,797,770 B2
(45) Date of Patent: Nov. 17, 2026

(54) METHODS FOR EXTRACTING MELATONIN

(71) Applicant: NUTRALAND USA, INC., Irvine, CA (US)

(72) Inventors: Ling Lin, Irvine, CA (US); Sanying Xu, Irvine, CA (US)

(73) Assignee: NUTRALAND USA, INC., Irvine, CA (US)

( * ) Notice: Subject to any disclaimer, the term of this patent is extended or adjusted under 35 U.S.C. 154(b) by 392 days.

(21) Appl. No.: 18/497,492

(22) Filed: Oct. 30, 2023

(65) Prior Publication Data

US 2025/0135377 A1 May 1, 2025

(51) Int. Cl.

*B01D 11/02* (2006.01)
*B01D 9/02* (2006.01)
*C07D 209/32* (2006.01)

(52) U.S. Cl.

CPC ............ *B01D 11/0288* (2013.01); *B01D 9/02* (2013.01); *B01D 11/0284* (2013.01); *C07D 209/32* (2013.01)

(58) Field of Classification Search

None
See application file for complete search history.

(56) References Cited

FOREIGN PATENT DOCUMENTS

| | | |
|---|---|---|
| CN | 106543068 | 3/2017 |
| CN | 113072479 | 7/2021 |
| CN | 115974756 A | 4/2023 |

OTHER PUBLICATIONS

Hu (CN 11302479—English translation)—Jul. 8, 2021.*

International Search Report mailed Dec. 19, 2024 in PCT/US2024/053186, filed Oct. 28, 2024.

Riga P, Medina S, García-Flores LA, Gil-Izquierdo Á. Melatonin content of pepper and tomato fruits: effects of cultivar and solar radiation. Food Chem. Aug. 1, 2014;156:347-52. Epub Feb. 12, 2014. PMID: 24629979.

Muszyńska B, Ekiert H, Kwiecień I, Maślanka A, Zodi R, Beerhues L. Comparative analysis of therapeutically important indole compounds in in vitro cultures of Hypericum perforatum cultivars by HPLC and TLC analysis coupled with densitometric detection. Nat Prod Commun. Oct. 2014;9(10):1437-40. PMID: 25522532.

Arnao MB, Hernández-Ruiz J. The Potential of Phytomelatonin as a Nutraceutical. Molecules. Jan. 22, 2018;23(1):238. doi: 10.3390/molecules23010238. PMID: 29361780; PMCID: PMC6017233.

Linde, K., et al., 'St. John's wort—an overview', Forschende Komplementärmedizin/Research in Complementary Medicine. 2009, vol. 16(3), pp. 146-155.

Reiter RJ, et al., "Phytomelatonin: assisting plants to survive and thrive." Molecules. Apr. 22, 2015;20(4):7396-437.

T. Herrera et al., "Teas and herbal infusions as sources of melatonin and other bioactive non-nutrient Components" LWT—Food Science and Technology, 89 (2018), 65-73.

Y. Byeon et al., "Predominance of 2-hydroxymelatonin over melatonin in plants." J Pineal Res. 2015; 59:448-484.

Yang TH, et al., "Dietary supplement of tomato can accelerate urinary aMT6s level and improve sleep quality in obese postmenopausal women." Clin Nutr. Jan. 2020;39(1):291-297.

Dehnavi P, et al., "Effect of Tomato (*Solanum lycopersicum*) Extract in Patients with Primary Insomnia: A Double-blind Randomized Study." Cent Nerv Syst Agents Med Chem. 2023;23(2):137-143.

* cited by examiner

*Primary Examiner* — Susan Hoffman

(74) *Attorney, Agent, or Firm* — KNOBBE, MARTENS, OLSON & BEAR, LLP

(57) ABSTRACT

Embodiments of the present disclosure relate to methods for extracting and purifying melatonin from natural melatonin sources. Such methods may include extracting melatonin from *Hypericum perforatum* or from tomatoes. Such methods may include mixing the melatonin source with a first solvent; filtering the extraction solution; and concentrating the filtrate to obtain coarse extract. Compositions of the melatonin extract obtained from the methods are also provided.

20 Claims, 2 Drawing Sheets

METHODS FOR EXTRACTING MELATONIN

BACKGROUND

Field

The present disclosure provides methods for extracting melatonin from natural sources such as *Hypericum perforatum* or tomatoes.

Description of the Related Art

*Hypericum perforatum* is a traditional Chinese herbal medicine with a bitter, astringent taste and a flat nature. *Hypericum perforatum* is commonly referred to as St. John's wort (SJW), and may also be known as Forsythia, Weeping Forsythia, and Thousand Layer Tower. It has the effects of soothing the liver and relieving depression, clearing heat and dampness, and reducing swelling and relieving pain. It is included in various local medicinal plant monographs and is listed in the Pharmacopoeia of the People's Republic of China (2005, 2010 edition). It may have anti-depression, anti-tumor, anti-viral, anti-bacterial, and anti-inflammatory functions. *Hypericum perforatum* has been widely developed and utilized globally, making it one of the three best-selling Chinese herbal medicines.

Melatonin (N-acetyl-5-methoxytruptamine) is a hormone secreted by the pineal gland. Melatonin, a strong endogenous free radical scavenger, has various physiological effects, such as regulating human circadian rhythm, improving human immunity, promoting normal metabolism of the endocrine system, and improving the body's antioxidant capacity. Melatonin is often a raw material for health food, and its application market is very broad. Most of the melatonin currently available on the market is produced via chemical synthesis.

Melatonin can be extracted from animals and plants. Plant generative organs (e.g., flowers, fruits), and especially seeds, have been proposed as having the highest melatonin concentrations, markedly higher than those found in vertebrate tissues. In this case it is called phytomelatonin, and it aids plants in terms of root growth, leaf morphology, chlorophyll preservation and fruit development. (Reiter R J, etc. Phytomelatonin: assisting plants to survive and thrive. Molecules. 2015 Apr. 22; 20 (4): 7396-437.) Melatonin has been detected in over a hundred plants, including hawthorn, bindweed, tomato, sour cherry, *Hypericum perforatum*, etc. (T. Herrera et al., LWT-Food Science and Technology, 89 (2018), 65-73). For example, Chinese Patent Application Number 201610845424.7 discusses a method for extracting melatonin from walnuts, while Chinese Patent Application Number 202110322825.5 discusses a method for extracting melatonin from the pineal gland of animals.

Extracting melatonin from *Hypericum perforatum* often results in high impurities in the product, including polyphenolic substances such as hyperoside and hypericin that are found in *Hypericum perforatum*. Hyperoside and hypericin are antidepressant components found in *Hypericum perforatum*. From a food safety standpoint, it may be desirable to remove and/or minimize hyperforin and hypericin when extracting melatonin from *Hypericum perforatum*.

In addition to melatonin, many plants, including *Hypericum perforatum*, also contain a certain amount of 2-hydroxymelatonin, as well as trace amounts of 4-hydroxymelatonin and 6-hydroxymelatonin, which are melatonin derivatives (Y. Byeon et al, J Pineal Res. 2015; 59:448-484). However, the separation and removal of 2-hydroxymelatonin and other melatonin derivatives from melatonin extracts has not been studied in detail.

The melatonin content in *Hypericum perforatum* varies depending on *Hypericum perforatum*'s origin, growth time, harvest time, and different parts of the plant (for example, the melatonin content in *Hypericum perforatum* flowers is dozens of times higher than that in leaves). Considering the low melatonin content in *Hypericum perforatum*, multi-utilization of the raw materials may be desirable. For example, after extracting melatonin, other effective components can also be extracted from *Hypericum perforatum*, which can help reduce the production cost of melatonin.

SUMMARY

The present disclosure provides methods of extracting melatonin from plant sources (*Hypericum perforatum* and tomatoes) and compositions of phytomelatonin produced by the methods described herein.

In one aspect, the present disclosure provides for a method for extracting melatonin from *Hypericum perforatum*, the method comprising:

(a) mixing *Hypericum perforatum* powder with a first solvent to produce an extraction solution;
(b) filtering the extraction solution to produce a filtered solution;
(c) concentrating the filtered solution to obtain a coarse extract of melatonin;
(d) crystallizing the coarse extract of melatonin to produce a crystallized solid;
(e) purifying the crystallized solid to obtain an intermediate product;
(f) dissolving the intermediate product in a second solvent to produce an intermediate solution; and
(g) heating and recrystallizing the intermediate solution to obtain a high purity melatonin extract comprising no less than 95% melatonin by weight. In some embodiments, the high purity melatonin extract comprises no less than 98.5% melatonin by weight.

In another aspect, the present disclosure provides for a method for extracting melatonin from tomatoes, the method comprising:

(a) mixing dried tomatoes with a first solvent to produce an extraction solution;
(b) filtering the extraction solution to produce a filtered solution;
(c) concentrating the filtered solution to produce a crude extract of melatonin;
(d) crystallizing the crude extract of melatonin in a second solvent two or more times to produce an intermediate tomato extract comprising at least 10% of melatonin by weight.

In some embodiments, the intermediate tomato extract has a melatonin content of about 15% to about 35% by weight. In some embodiment, the method further comprises (e) diluting the intermediate tomato extract with one or more excipients to yield a final tomato extract comprising at least 5% melatonin by weight.

In another aspect, the present disclosure provides for compositions of phytomelatonin obtained by the methods described herein.

DETAILED DESCRIPTION

Figure 1:
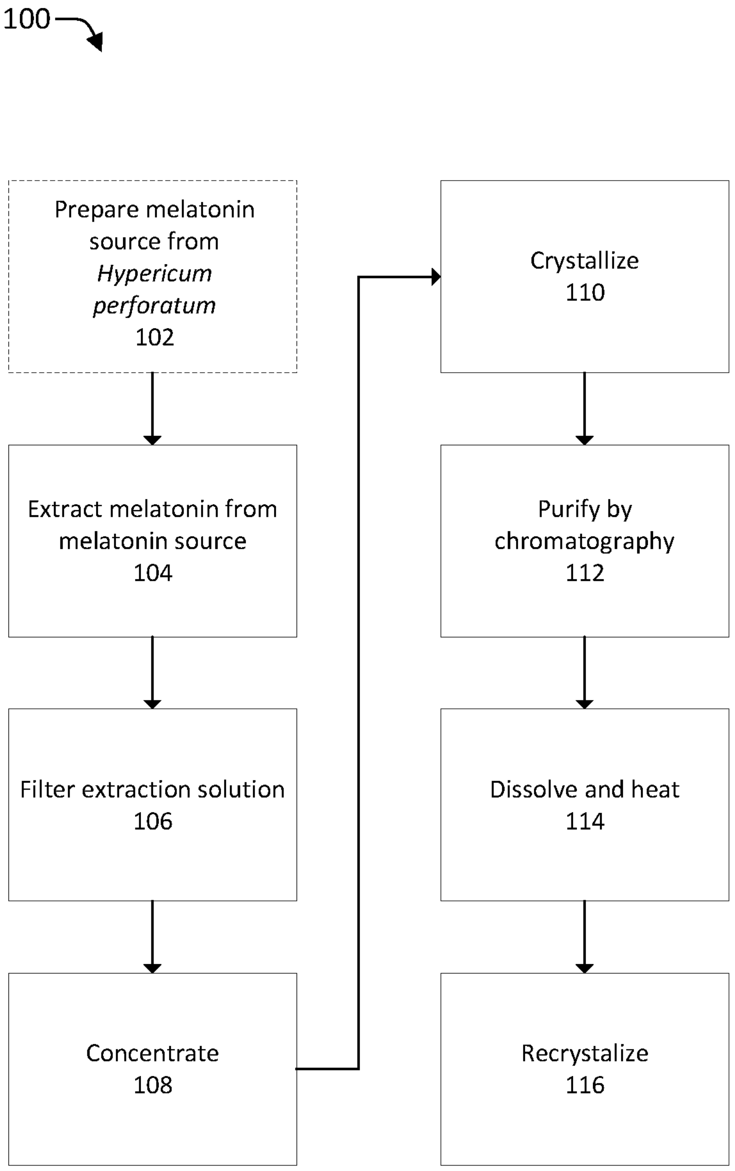
FIG. 1 illustrates a method of extracting melatonin from a melatonin source accordingly to certain embodiments of the present disclosure. As an example, melatonin may be extracted from *Hypericum perforatum* in accordance with the method of FIG. 1.

The present disclosure provides for a method for extracting melatonin from natural plants. Specifically, the present disclosure provides for a method for extracting high-purity natural melatonin from *Hypericum perforatum* and from tomatoes. This method can remove impurities such as hyperoside, hyperforin and hypericin, and melatonin derivatives such as 2-hydroxymelatonin, allowing for safe melatonin extracts. Melatonin produced from tomatoes may not include such impurities.

Method of Extracting Melatonin from *Hypericum perforatum*

An aspect of the present disclosure relates to a method for extracting melatonin from *Hypericum perforatum*, the method comprising:

(a) mixing a *Hypericum perforatum* powder with a first solvent to produce an extraction solution;

(b) filtering the extraction solution to produce a filtered solution;

(c) concentrating the filtered solution to produce a coarse extract;

(d) crystallizing the coarse extract to produce a crystallized solid;

(e) purifying the crystallized solid to obtain an intermediate product;

(f) dissolving the intermediate product in a second solvent to produce an intermediate solution; and (g) recrystallizing the intermediate solution to obtain a high purity melatonin extract. In some embodiments, the high purity melatonin extract comprises no less than 95% melatonin by weight. In some embodiments, the melatonin extract comprises no less than 98.5% melatonin by weight. In some embodiments, the high purity melatonin extract comprises no more than 1% 2-hydroxymelatonin by weight. In some embodiments, the high purity melatonin extract comprises no more than 100 ppm hyperforin. In further embodiments, the high purity melatonin extract comprises no more than 10 ppm hyperforin. In some embodiments, the high purity melatonin extract comprises no more than 100 ppm hypericin. In further embodiments, the high purity melatonin extract comprises no more than 10 ppm hypericin.

In some embodiments, step (a) comprises mixing the *Hypericum perforatum* powder and the first solvent at 40° C. to 85° C. In some embodiments, step (a) comprises mixing for 0.5 to 8 hours. In some embodiments, the first solvent comprises or is ethanol. In some embodiments, the first solvent has a mass about 3 to 10 times the mass of the *Hypericum perforatum* powder. In further embodiments, the first solvent has a mass of about 5 to 7 times the mass of the *Hypericum perforatum* powder. In further embodiments, the first solvent has a mass of 5 to 6 times the mass of the *Hypericum perforatum* powder. In further embodiments, step (a) comprises mixing the *Hypericum perforatum* at 70° C. to 80° C. In further embodiments, step (a) comprises mixing for 4 to 6 hours. In some embodiments, step (a) comprises mixing the *Hypericum perforatum* powder and the first solvent at 40° C., 41° C., 42° C., 43° C., 44° C., 45° C., 46° C., 47° C., 48° C., 49° C., 50° C. 51° C., 52° C., 53° C., 54° C., 55° C., 56° C., 57° C. 58° C., 59° C., 60° C., 61° C., 62° C., 63° C., 64° C., 65° C., 66° C., 67° C., 68° C., 69° C., 70° C., 71° C., 72° C. 73° C. 74° C. 75° C. 76° C., 77° C., 78° C., 79° C., 80° C., 81° C., 82° C., 83° C., 84° C., or 85° C., or in a range defined by any two of the preceding values. In some embodiments, step (a) comprises mixing the *Hypericum perforatum* powder and the first solvent for 0.5, 1, 1.5, 2, 2.5, 3, 3.5, 4, 4.5, 5, 5.5, 6, 6.5, 7, 7.5, or 8 hours or in a range defined by any two of the preceding values. In some embodiments, the first solvent has a mass 3, 3.5, 4, 4.5, 5, 5.5, 6, 6.5, 7, 7.5, 8, 8.5, 9, 9.5, or 10 times the mass of the *Hypericum perforatum* powder or in a range defined by any two of the preceding values.

In some embodiments, step (d) comprises dissolving the coarse extract of melatonin in a water-saturated ethyl acetate solution having a pH from about 7.5 to about 9. In some embodiments, the ethyl acetate has a mass about 0.2-2 times the mass of the coarse extract. In some embodiments, step (d) includes lowering the temperature of the mixture to −10° C. to 25° C. while stirring for about 0.5 to 10 hours. In further embodiments, the pH of the water-saturated ethyl acetate is from about 8 to about 8.5. In further embodiments, the mass of the ethyl acetate added to the coarse extract of melatonin is preferably 0.5 to 1 times the mass of the coarse extract. In some further embodiments, step (d) comprises lowering the temperature of the mixture to 0° C. to 5° C., the duration of the crystallizing being 4 to 5 hours. In some embodiments, the crystallized solid comprises less than or no more than 100, 90, 80, 70, 60, 50, 40, 30, 20, 10 or 5 ppm of hyperforin. In some embodiments, the crystallized solid comprises no more than or less than 10 ppm of hyperforin. In some embodiments, the crystallized solid comprises less than or no more than 100, 90, 80, 70, 60, 50, 40, 30, 20, 10 or 5 ppm of hypericin. In some embodiments, the crystallized solid comprises no more than or less than 10 ppm of hypericin. In some embodiments, the method comprises dissolving the crystalized solid and repeating step (d) such that the crystallized solid comprises less than 100 ppm of hyperforin and less than 100 μm hypericin. In some embodiments, the water-saturated ethyl acetate has a mass of 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2 times the mass of the coarse extract, or in a range defined by any two of the preceding values. In some embodiments, the ethyl acetate saturated with water has a pH of 7.5, 7.6, 7.7, 7.8, 7.9, 8.0, 8.1, 8.2, 8.3, 8.4, 8.5, 8.6, 8.7, 8.8, 8.9, or 9.0, or in a range defined by any two of the preceding values. In some embodiments, step (d) comprises lowering the temperature of the mixture to −10° C., −9° C., −8° C., −7° C., −6° C., −5° C., −4° C., −3° C., −2° C., −1° C., 0° C. 1° C., 2° C., 3° C., 4° C., 5° C., 6° C., 7° C., 8° C., 9° C., 10° C., 11° C., 12° C., 13° C., 14° C., 15° C., 16° C., 17° C. 18° C., 19° C., 20° C., 21° C. 22° C., 23° C., 24° C., or 25° C., or in a range defined by any two of the preceding values. In some embodiments, the crystallized solid comprises no more than or less than about 10, 20, 30, 40, 50, 55, 60, 65, 70, 75, 80, 85, 90, 95, 100, 105, 110, 115, 120, 125, 130, 135, 145, or 150 ppm of hyperforin or hypericin, or in a range defined by any two of the preceding values.

In some embodiments, step (e) includes purifying the crystallized solid using column chromatography. In further embodiments, step (e) includes purifying the crystallized solid using silica gel column chromatography. In some embodiments, the column chromatography purification comprises eluting with petroleum ether, ethyl acetate, ethanol or a combination thereof. In some embodiments, the mass of the silica gel used in step (e) is 10 to 100 times the mass of the intermediate product, and wherein the size of silica gel particles applied is about 60 to 400 mesh. In some embodiments, step (e) comprises use of an elution solvent with the silica gel column, the elution solvent comprising petroleum ether, ethyl acetate, and or ethanol. In further embodiments, the elution solvent is a mixed solvent of petroleum ether, ethyl acetate, and ethanol, wherein the ratio of ethyl acetate to ethanol is about 3:1. In yet further embodiments, the intermediate product comprises no more than 1.0% 2-hydroxymelatonin. In some embodiments, the mass of the silica gel used in step (c) is 10, 20, 30, 40, 50, 60, 70, 80, 90, or 100 times the mass of the intermediate product, or in a range defined by any two of the preceding values. In some embodiments, the size of silica gel particles is about 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mesh, or in a range defined by any two of the preceding values.

In some embodiments, step (f) comprises dissolving the intermediate product in about 5% to about 50% aqueous ethanol solution, wherein the mass of the ethanol solution is about 10 to 50 times the mass of the intermediate product, and the heating comprises heating the solution until the solution is clear. In some further embodiments, the second solvent comprises a 20% to 25% ethanol-water solution. In some embodiments, step (f) comprises dissolving the intermediate product in about 5%, 10%, 15%, 20%, 25%, 30%, 35%, 40%, 45%, or 50% aqueous ethanol solution, or in a range defined by any two of the preceding values. In some embodiments, the mass of the ethanol solution is about 10, 20, 30, 40, or 50 times the mass of the intermediate product, or in a range defined by any two of the preceding values.

In some embodiments, step (g) comprises recrystallizing the intermediate solution at 0° C. to 30° C. In some embodiments, the duration of the recrystallizing is about 4 to 48 hours. In further embodiments, step (g) comprises recrystallizing the intermediate solution at about 5° C. to 10° C. for 20 to 24 hours. In some embodiments, the mass of the second solvent is 25 to 30 times that of the intermediate product. In some examples, step (g) comprises recrystallizing the solution at 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C., or in a range defined by any two of the preceding values. In some embodiments, the recrystallization lasts about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours, or in a range defined by any two of the preceding values. In some embodiments, the mass of the second solvent is 25, 26, 27, 28, 29, or 30 times the mass of the intermediate product, or in a range defined by any two of the preceding values.

In some embodiments, the high-purity melatonin extract comprises no more than 100 ppm hyperforin, no more than 100 ppm hypericin, and/or no more than 1.0% 2-hydroxymelatonin. In some embodiments, the melatonin extract comprises no more than 10 ppm hyperforin. In some embodiments, the melatonin extract comprises no more than 10 ppm hypericin. In some embodiments, the method comprises crushing dried *Hypericum perforatum* to produce the *Hypericum perforatum* powder. In some embodiments, the high-purity melatonin extract comprises no more than 1.0% 2-hydroxymelatonin by mass. In some embodiments, the melatonin extract comprises less than or no more than 5, 10, 15, 20, 25, 30, 35, 40, 45, 50, 55, 60, 65, 70, 75, 80, 85, 90, 95, 100, 105, 110, 115, 120, 125, 130, 135, 145, or 150 ppm of hyperforin or hypericin, or in a range defined by any two of the preceding values. In some embodiments, the intermediate product comprises no more than 0.1%, 0.2%, 0.3%, 0.4%, 0.5%, 1.0%, 1.5%, 2.0%, 2.5%, 3.0%, 3.5%, 4.0%, 4.5%, or 5.0% 2-hydroxymelatonin by mass, or in a range defined by any two of the preceding values.

FIG. 1 illustrates an example process 100 for purifying melatonin from a melatonin source in accordance with the present disclosure. In some embodiments, the melatonin source is *Hypericum perforatum*. Melatonin may be extracted from *Hypericum perforatum* using the process 100 in accordance with the present disclosure.

At step 102, optionally prepare the melatonin source. In some embodiments, step 102 comprises powdering *Hypericum perforatum*. In such embodiments, step 102 may comprise cleaning and drying the *Hypericum perforatum*.

At step 104, extract melatonin from the melatonin source. In some embodiments, step 104 may include mixing the prepared melatonin source with a first solvent to produce an extraction solution. In some embodiments, step 104 includes mixing the *Hypericum perforatum* powder and the first solvent at 40° C. to 85° C. for 0.5 to 8 hours. In some embodiments, the first solvent is ethanol and wherein the first solvent has a mass 3-10 times the mass of the *Hypericum perforatum* powder. In some embodiments, step 104 may include mixing the *Hypericum perforatum* at 70° C. to 80° C., for 4 to 6 hours.

At step 106, filter the extraction solution to produce a filtered solution.

At step 108, concentrate the filtered solution to obtain a coarse extract of melatonin.

At step 110, crystalize the coarse extract to produce a crystallized solid. In some embodiments, step 110 comprises introducing ethyl acetate saturated with water to the coarse extract, the ethyl acetate having a mass 0.2-2 times the mass of the coarse extract, and ethyl acetate saturated with water has a pH of from 7.5 to 9.0, lowering the temperature of the mixture to −10° C. to 25° C. while stirring for 0.5 to 10 hours. In further embodiments, the pH of the ethyl acetate saturated with water is from 8 to 8.5, wherein the mass of the ethyl acetate added to the coarse extract of melatonin is preferably 0.5 to 1 times the mass of the coarse extract, wherein the crystallizing comprises lowering the temperature of the mixture to 0° C. to 5° C., the duration of the crystallizing being 4 to 5 hours. In some embodiments, wherein the crystallized solid comprises no more than 100 ppm of hyperforin, no more than 100 ppm of hypericin. In some embodiments, the method comprises dissolving the crystalized solid and repeating step 110.

At step 112, purify the crystalized solid to obtain an intermediate product. In some embodiments, step 112 includes purifying the crystalized solid via chromatography, for example silica gel column chromatography. In some embodiments involving silica gel column chromatography, step 112 can include eluting with petroleum ether, ethyl acetate, ethanol or a combination thereof. In some embodiments involving silica gel column chromatography, the mass of the silica gel used is 10 to 100 times the mass of the intermediate product, and the number of silica gel particles applied is 60 to 400 mesh. In some embodiments, step 112 comprises use of an elution solvent with the silica gel column, the elution solvent comprising petroleum ether, ethyl acetate, and or ethanol. In further embodiments, the elution solvent is a mixed solvent of petroleum ether, ethyl acetate, and ethanol, wherein the ratio of ethyl acetate to ethanol is 3:1. In yet further embodiments, the intermediate product comprises no more than 1.0% 2-hydroxymelatonin.

At step 114, dissolve and heat the intermediate product. The intermediate product may be dissolved in a second solvent, and subsequent heating of the mixture can produce an intermediate solution. In some embodiments, step 114 includes dissolving the intermediate product in 5%-50% aqueous ethanol solution, wherein the mass of the ethanol solution is 10 to 50 times the mass of the intermediate product, and the heating comprises heating the solution until the solution is clear. In some embodiments, the second solvent comprises a 20%-25% by volume ethanol-water solution.

At step 116, crystalize the intermediate product. This step is also referred to herein as "recrystallization" or "recrystallizing." In some embodiments, step 116 comprises recrystallizing the solution at 0° C. to 30° C. for 4 to 48 hours. In further embodiments, step 116 comprises recrystallizing the solution at 5° C. to 10° C. for 20-24 hours, and wherein the mass of the second solvent is 25-30 times that of the intermediate product.

Method of Extracting Melatonin from Tomatoes

Another aspect of the present disclosure relates to a method for extracting melatonin from tomatoes, the method comprising:

(a) mixing dried tomatoes with a first solvent to produce an extraction solution;
(b) filtering the extraction solution to produce a filtered solution;
(c) concentrating the filtered solution to obtaining a crude extract of melatonin; and
(d) crystallizing the crude extract of melatonin in a second solvent two or more times to produce an intermediate tomato extract comprising at least 10% melatonin by weight. In some further embodiments, the intermediate tomato extract comprising at least 11%, 12%, 13%, 14% or 15% melatonin by weight.

In some embodiments, the method further comprises: (e) diluting the intermediate tomato extract with one or more excipients to yield a final tomato extract comprising at least 5% melatonin by weight. In further embodiments, the one or more excipients comprises tapioca maltodextrin. In some embodiments, the melatonin content of the diluted extract may be at least 2.5%, 3.0%, 3.5%, 4.0%, 4.5%, 5.0%, 5.1%, 5.2%, 5.3%, 5.4%, 5.5%, 5.6%, 5.7%, 5.8%, 5.9%, or 6.0% by weight, or in a range defined by any two of the preceding values.

In some embodiments, the method further comprises drying fresh tomatoes to produce the dried tomatoes.

In some embodiments, step (a) comprises heating the mixture to a temperature ranging from about 40° C. to about 85° C. In some embodiments, the duration of step (a) is from about 0.5 to about 12 hours. In some embodiments, the first solvent is about 80% to 98% or 90% to 96% ethanol. In some embodiments, the mass of the first solvent is 1 to 10 times the mass of the tomatoes. In some embodiments, step (a) comprises stirring. In some embodiments, step (a) comprises mixing the tomatoes with the first solvent at 40° C., 41° C., 42° C. 43° C., 44° C., 45° C., 46° C., 47° C., 48° C., 49° C., 50° C., 51° C., 52° C., 53° C., 54° C., 55° C., 56° C. 57° C., 58° C. 59° C., 60° C., 61° C., 62° C., 63° C., 64° C., 65° C., 66° C., 67° C., 68° C. 69° C., 70° C., 71° C. 72° C. 73° C. 74° C., 75° C., 76° C. 77° C., 78° C. 79° C., 80° C., 81° C., 82° C., 83° C., 84° C., or 85° C., or in a range defined by any two of the preceding values. In some embodiments, step (a) comprises mixing the tomatoes with the first solvent for 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 hours or in a range defined by any two of the preceding values. In some embodiments, the first solvent may be 90%, 91%, 92%, 93%, 94%, 95%, or 96% ethanol, or in a range defined by any two of the preceding values. In some embodiments, the mass of the first solvent may be 1, 2, 3, 4, 5, 6, 7, 8, 9, or 10 times the mass of the tomatoes, or in a range defined by any two of the preceding values.

In some embodiments, step (d) is repeated by recrystallization for 1, 2, or 3 times. In some such embodiments, the second solvent comprises or is about 10% to 30% ethanol. In some further embodiments, the second solvent is of 1 to 50 times the mass of the crude melatonin extract. In some embodiments, the second solvent includes 10%, 15%, 20%, 25%, or 30% ethanol, or ethanol in a range defined by any two of the preceding values. In some embodiments, the second solvent is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 29, or 50 times the mass of the crude melatonin extract, or in a range defined by any two of the preceding values.

In some embodiments, step (d) occurs at a temperature ranging from about −10° C. to 25° C. In some embodiments, step (d) occurs at a temperature of 10° C., 11° C., 12° C., 13° C., 14° C., 15° C., 16° C., 17° C., 18° C., 19° C., 20° C., 21° C., 22° C., 23° C., 24° C., or 25° C., or in a range defined by any two of the preceding values.

In some embodiments, the intermediate tomato extract comprises a melatonin content of about 15% to 35% by weight. In some embodiments, the intermediate tomato extract comprises a melatonin content of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35% by weight, or within a range defined by any two of the preceding values.

In some embodiments, the method may further comprise: (e) diluting the intermediate tomato extract with one or more excipients to yield a final tomato extract comprising at least 5%, 6%, 7%, or 8% melatonin by weight. In some such embodiments, the one or more excipients comprises a bulking agent or a thickening agent, such as tapioca maltodextrin.

Figure 2:
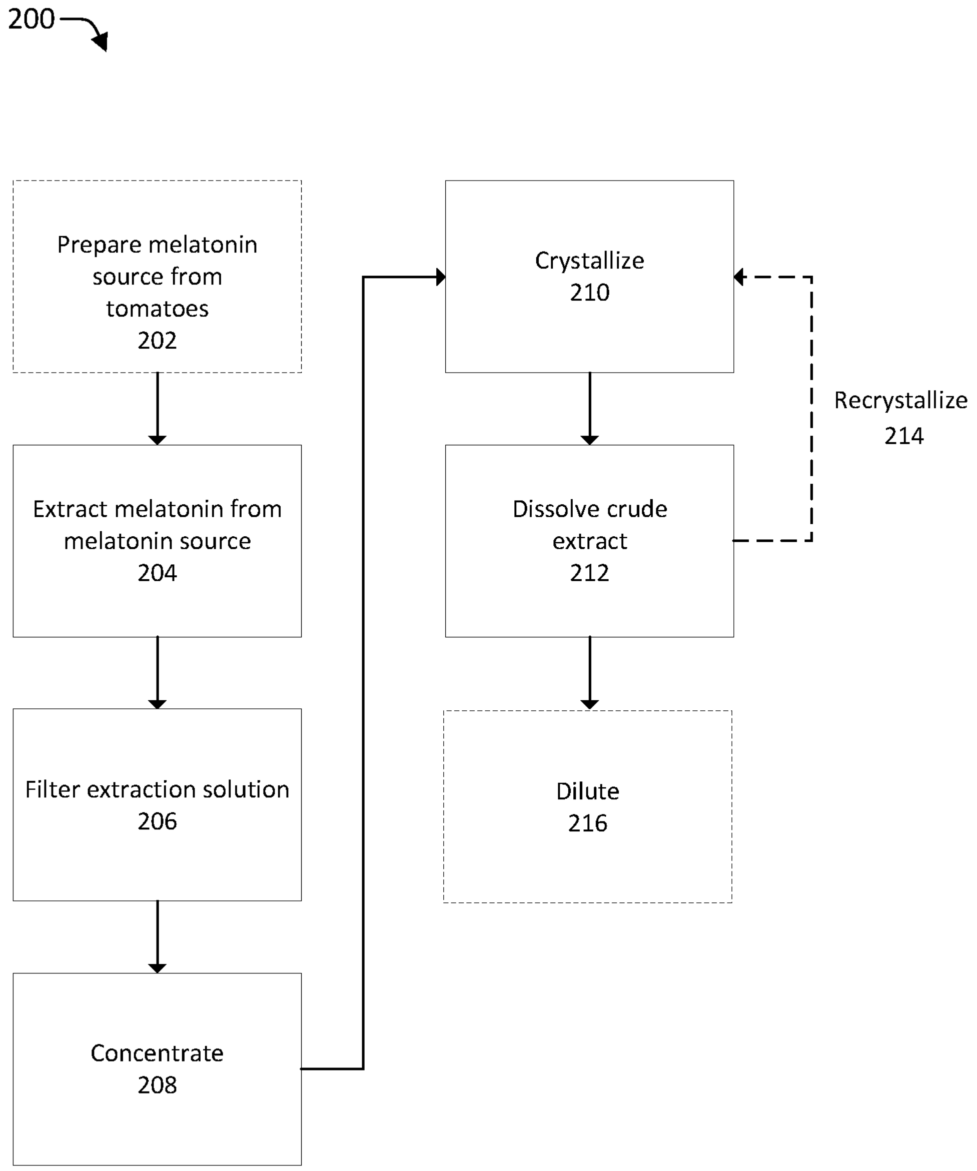
FIG. 2 illustrates a method of extracting melatonin from a melatonin source accordingly to certain embodiments of the present disclosure. As an example, melatonin may be extracted from tomatoes in accordance with the method of FIG. 2.

FIG. 2 illustrates an example process 200 for purifying melatonin from a melatonin source in accordance with the present disclosure. In some embodiments, tomatoes are the melatonin source. Melatonin may be extracted from tomatoes using the process 200 in accordance with the present disclosure.

At step 202, optionally prepare the melatonin source. The melatonin source may include tomatoes. The tomatoes may be fresh and/or ripe. Step 202 may include drying the tomatoes.

At step 204, extract melatonin from the melatonin source. Step 204 may include mixing the melatonin source with a first solvent. In some embodiments, step 204 comprises heating the mixture to a temperature ranging from 40° C. to 85° C. for 0.5 to 12 hours, wherein the first solvent is 90% to 96% ethanol, and wherein the mass of the first solvent is 1 to 10 times the mass of the tomatoes. In some embodiments, step (a) comprises stirring.

At step 206, filter the extraction solution to produce a filtered solution.

At step 208, concentrate the filtered solution to obtain a crude extract of melatonin.

At step 210, crystalize the crude extract to produce a melatonin concentrate. In some embodiments, step 210 may occur at a temperature ranging from about −10° C. to 25° C.

At step 212, dissolve the melatonin concentrate in a second solvent. Step 210 and step 212 may optionally be repeated (recrystallization 214) one or more times. Step 212 and recrystallization 214 may occur at a temperature ranging from about −10° C. to 25° C. In some embodiments, the extract after one or more recrystallization 214 (i.e., two or more crystallization steps) comprises a high concentration melatonin content of 15% to 35% by weight.

At step 216, optionally dilute the high concentration melatonin extract. In some embodiments, step 216 includes diluting the melatonin extract to a melatonin content of at least 5% by weight. In some embodiments, step 216 may include mixing, drying, sterilizing, and sifting the melatonin extract with additives to obtain a diluted extract. In some further embodiments, the additives may include one or more food-grade excipients selected from a bulking agent, a thickening agent, a carrier and a texturize, or combinations thereof. In some embodiments, the additives may include tapioca maltodextrin.

Compositions of Melatonin from *Hypericum perforatum*

In another aspect, the present disclosure provides for compositions including melatonin, for example, melatonin extract obtained from *Hypericum perforatum* as described herein. In some such embodiments, the melatonin extract comprises no less than 90%, 91%, 92%, 93%, 94%, 95%, 95.5%, 96%, 96.5%, 97%, 97.5%, 98%, or 98.5% melatonin by weight. In some embodiments, the melatonin extract comprises no more than 100 ppm hyperforin, no more than 100 ppm hypericin, and no more than 1.0% 2-hydroxymelatonin. In some embodiments, the melatonin extract comprises no more than 10 ppm hyperforin. In some embodiments, the melatonin extract comprises no more than 10 ppm hypericin.

Compositions of Melatonin from Tomatoes

In another aspect, the present disclosure provides a composition of melatonin as a tomato extract as described herein. In some embodiments, the tomato extract may comprise a melatonin content of about or at least about 10% to about 50% by weight. In some embodiments, the tomato extract comprises a melatonin content of at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35% by weight, or within a range defined by any two of the preceding values. In some further embodiments, one or more additives may be added to the tomato extract with high concentration of melatonin to provide a final product containing at least 5% by weight of melatonin. In some such embodiments, the additives may include one or more food-grade excipients selected from a bulking agent, a thickening agent, a carrier and a texturizer, or combinations thereof. Non-limiting examples of bulking agents include soluble fibers, dietary fibers, oligosaccharides, polydextrose, inulin, cellulose and derivatives, beta-glucan, resistant starch, hydrocolloids, and arabinogalactan, etc. Non-limiting examples of food thickeners include corn starch, potato starch, xanthan gum, arrowroot, agar, gelatin, pectin, carrageenan, tapioca starch, gum arabic, sodium alginate, carboxymethylcellulose, modified starch, gum tragacanth, polysaccharides, etc. In some embodiments, the additive comprises tapioca maltodextrin.

EXAMPLES

Various aspects of the present disclosure are described in detail in conjunction with the following examples. Such examples are provided for illustrative purposes and are not intended to be an extensive list of all possible implementations in accordance with the present disclosure. Based on the examples herein, all other implementation examples obtained by those skilled in the art without creative labor are within the scope of the present disclosure.

Example 1—Rough Product Purity—*Hypericum perforatum*

*Hypericum perforatum* (flowering top) was cleaned and dried. *Hypericum perforatum* were ground into powder. 105 kg of the powder was mixed with 630 kg of ethanol (6× the mass of *Hypericum perforatum* powder). The mixture was heated to about 80° C. and stirred for 6 hours. The mixture was filtered to remove the insoluble material. The filtrate was concentrated to yield 1.1 kg coarse extract of melatonin. The coarse extract was dissolved in 1.1 kg of water-saturated ethyl acetate (1× the mass of coarse extract) with a pH of 8.0 at 5° C. and left to crystallize for 4 hours. After crystallization, the mixture was filtered and dried under vacuum to obtain 81 g of rough product of melatonin. A HPLC detection showed that the intermediate product of melatonin contained 8.1 ppm of hyperforin and 4.3 ppm of hypericin.

Example 2—Rough Product Purity—*Hypericum perforatum*

*Hypericum perforatum* (flowering top) was cleaned, dried, and crushed into a powder. 490 kg of ethanol (5× the mass of the crushed *Hypericum perforatum*) was added to 98 kg of crushed *Hypericum perforatum*. The mixture was heated to about 70° C. and stirred for 6 hours. The mixture was filtered to remove insoluble material. The filtrate was concentrated to obtain 0.92 kg coarse extract of melatonin. The coarse extract of melatonin was crystallized using ethyl acetate saturated with 0.92 kg water (1× times mass of the coarse extract) at a pH of 8.5 and cooled to 0° C. for 4 hours. After crystallization, the mixture was filtered and dried under vacuum to obtain 68 g of rough product of melatonin. A HPLC detection showed that the rough product of melatonin contained 1.1 ppm of hyperforin and no detectable hypericin.

Example 3—Chromatographic Purification—*Hypericum perforatum*

A column chromatography using 40 kg of silica gel and eluted with a mixture of ethyl acetate and ethanol in a volume ratio of 3:1 was performed on 1.03 kg of rough product of melatonin. The flow rate was controlled and continuously monitored to ensure that the melatonin flowed out first and the 2-hydroxymelatonin remained on the silica gel column. The melatonin fraction was concentrated to obtain 656 g semi-finished product of melatonin. The content of 2-hydroxymelatonin in the semi-finished product of melatonin was 0.43%.

Example 4—Chromatographic Purification—*Hypericum perforatum*

10.06 kg of rough product of melatonin was subjected to column chromatography on 100 mesh silica gel (400 kg) and eluted with a mixed solvent of ethyl acetate and ethanol (3:1, v/v). Flow rate was controlled, and eluate was continuously monitored to ensure that the melatonin fraction was eluted first and the 2-hydroxymelatonin was retained on the silica gel column. The melatonin fraction was concentrated to obtain 7.45 kg of semi-finished product of melatonin, with 0.89% 2-hydroxymelatonin content detected.

Example 5—Crystallization at 10° C. for 20 Hours—*Hypericum perforatum*

5.1 kg of rough product of melatonin was heated and dissolved in 150 kg of 20% ethanol aqueous solution, cooled to 10° C. and allowed to crystallize for 20 hours. The crystals were filtered and then were dried. The crystal was tested to contain 32.5 ppm of hyperforin, 16.6 ppm of hypericin, 0.78% of 2-hydroxymelatonin, and 99.1% of melatonin, with a crystal weight of 3.87 kg.

Example 6—Crystallization at 5° C. for 24 Hours—*Hypericum perforatum*

5.1 kg of rough product of melatonin was heated and dissolved in 150 kg of 25% ethanol aqueous solution, cooled to 5° C. and allowed to crystallize for 24 hours. The crystals were filtered, and then were dried. The crystal was tested to contain 7.6 ppm of hyperforin, no hypericin was detected, 0.27% of 2-hydroxymelatonin, and 99.5% of melatonin, with a crystal weight of 3.28 kg.

Example 7—Comparative Example of *Hypericum perforatum* Extraction

Ethanol (490 kg) 5 times the mass of crushed *Hypericum perforatum* was added to 98 kg of crushed *Hypericum perforatum* (flowering top), heated to about 80° C., and stirred for 6 hours to extract. After filtering out the insoluble substances, the filtrate was concentrated to obtain 0.9 kg of coarse extract of melatonin. The coarse extract of melatonin was crystallized with ethyl acetate (0.9 kg) equal to the mass of coarse extract at 0° C. for 6 hours. The crystallization mixture was filtered. The crystals were vacuum-dried to obtain 89 g of rough product of melatonin. HPLC analysis showed that the rough product of melatonin contained 1400 ppm of hyperforin and 760 ppm of hypericin.

Example 8—Extraction from Dried Tomatoes

95% ethanol (1500 L) was added to 500 kg of dried tomatoes. The mixture underwent reflux extraction for 2 hours. The mixture was filtered. The filtrate obtained was concentrated to approximately 12 kg of crude paste (also referred to herein as a coarse extract or crude extract). The crude paste was purified through three crystallization steps at −10° C. using 25% ethanol. Purification yielded a concentrate with 31% melatonin content. The concentrate was then mixed, dried, sterilized, and sifted with additives, including tapioca maltodextrin, to obtain a powdered tomato extract with 5.5% melatonin and 0.12% lycopene content as verified through HPLC.

Example 9—Extraction from Fresh Tomatoes

Fresh, ripe tomatoes were physically dried to obtain dried tomatoes. 90% Ethanol 5 times the mass of the dried tomatoes was added for a six-hour reflux extraction. The mixture was filtered. After filtration, the filtrate was vacuum concentrated to obtain a crude melatonin extract (also referred to herein as a coarse extract). The crude melatonin extract was crystallized twice with 15% ethanol. The obtained concentrate was dried to yield a melatonin concentrate with 18% content. This concentrate was further diluted, mixed, dried, sterilized, and sifted with an appropriate amount of tapioca maltodextrin to obtain a melatonin extract with 5.1% melatonin content.

Example 10—Altered Reflux Extraction—Tomato 500 kg of dried tomatoes are added to 1000 liters of 96% ethanol. The mixture was heated and reflux extracted at 60° C. for four hours. The extract was filtered and concentrated to approximately 10 kg of crude paste (also referred to herein as a coarse extract). The crude paste was subjected to three crystallization steps at −10° C. using 10% ethanol to yield a concentrate with 34% melatonin content. This concentrate was then mixed, dried, sterilized, and sifted with additives, including tapioca maltodextrin, to obtain a tomato extract with 5.4% melatonin content.

Example 11—Different Varieties of Tomato

With respect to Example 8, different varieties of dried tomatoes were chosen for the same method of melatonin extraction. Although the extraction efficiency varied slightly between different tomato varieties, the tomato extract obtained through the method of Example 8 generally contains over 5% melatonin.

Terminology

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an," and "the" include plural referents unless the context clearly dictates otherwise. Unless otherwise indicated, conventional methods of mass spectroscopy, NMR, and HPLC are employed. The use of "or" or "and" means "and/or" unless stated otherwise. Furthermore, use of the term "including" as well as other forms, such as "include." "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, "recovery rate" is the proportion of a component that is isolated from a raw material containing that component divided by the total amount of that component originally present in the raw material. For example, "extraction recovery rate of melatonin from the melatonin source" refers to the proportion of (melatonin isolated from the melatonin source) to (melatonin originally present in the melatonin source). Recovery rate can be used to describe a single step of an extraction process, several steps of an extraction process, or an extraction process as a whole.

Embodiments have been described in connection with the accompanying drawings. In addition, the foregoing embodiments have been described at a level of detail to allow one of ordinary skill in the art to make and use the devices, systems, methods, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, for example, "can." "could," "might." "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

Language of degree used herein, such as the terms "approximately," "about," "generally." and "substantially" represent a value, amount, or characteristic close to the stated value, amount, or characteristic that still performs a desired function or achieves a desired result.

It is to be understood that the ranges provided herein include the stated range and any value or sub-range within the stated range, as if such value or sub-range were explicitly recited. For example, a range from about 60° C. to about 85° C. should be interpreted to include not only the explicitly recited limits of from about 60° C. to about 85° C., but also to include individual values, such as about 80.5° C., about 68° C., about 61.2° C., etc., and sub-ranges, such as from about 75° C. to about 80° C., etc.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, engines, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

While the above detailed description has shown, described, and pointed out novel features as applied to various embodiments, it will be understood that various omissions, substitutions, and changes in the form and details of the methods and compositions illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method for extracting melatonin from *Hypericum perforatum*, the method comprising:

(a) mixing a *Hypericum perforatum* powder with a first solvent to produce an extraction solution;

(b) filtering the extraction solution to produce a filtered solution;

(c) concentrating the filtered solution to obtain a coarse extract of melatonin;

(d) crystallizing the coarse extract of melatonin to produce a crystallized solid;

(e) purifying the crystallized solid to obtain an intermediate product;

(f) dissolving the intermediate product in a second solvent to produce an intermediate solution; and (g) recrystallizing the intermediate solution at about 0° C. to about 30° C. to obtain a high purity melatonin extract comprising no less than 95% melatonin by weight.

2. The method of claim 1, wherein the high purity melatonin extract comprises no more than 1% 2-hydroxymelatonin by weight.

3. The method of claim 1, wherein the high purity melatonin extract comprises no more than 100 ppm hyperforin and no more than 100 ppm hypericin.

4. The method of claim 1, wherein step (a) comprises mixing the *Hypericum perforatum* powder and the first solvent at about 40° C. to about 85° C., and wherein the first solvent is ethanol.

5. The method of claim 4, wherein the first solvent has a mass about 3 to about 10 times the mass of the *Hypericum perforatum* powder.

6. The method of claim 1, wherein step (d) comprises dissolving the coarse extract of melatonin in a water-saturated ethyl acetate solution having a pH from about 7.5 to about 9.

7. The method of claim 6, wherein the water-saturated ethyl acetate solution is about 0.2 to about 2 times the mass of the coarse extract of melatonin.

8. The method of claim 6, where the crystallization is carried out at about −10° C. to about 25° C.

9. The method of claim 1, wherein the crystallized solid in step (d) comprises no more than 100 ppm of hyperforin, and no more than 100 ppm of hypericin.

10. The method of claim 1, wherein step (e) is performed using column chromatography.

11. The method of claim 1, wherein the intermediate product of step (e) comprises no more than 1.0% 2-hydroxymelatonin by weight.

12. The method of claim 1, wherein step (f) comprises dissolving the intermediate product in about 5% to about 50% aqueous ethanol solution.

13. The method of claim 12, wherein the mass of the aqueous ethanol solution is about 10 to about 50 times the mass of the intermediate product.

14. The method of claim 2, wherein step (d) comprises dissolving the course extract of melatonin in a water-saturated ethyl acetate solution having a pH from about 7.5 to about 9.

15. The method of claim 14, wherein the water-saturated ethyl acetate solution is about 0.2 to about 2 times of the mass of the coarse extract of melatonin.

16. The method of claim 14, wherein the crystallization is carried out at about −10° C. to about 25° C.

17. The method of claim 2, wherein step (e) is performed using column chromatography.

18. The method of claim 17, wherein the intermediate product of step (e) comprises no more than 1.0% 2-hydroxymelatonin by weight.

19. The method of claim 2, wherein step (f) comprises dissolving the intermediate product in about 5% to about 50% aqueous ethanol solution.

20. The method of claim 19, wherein the mass of the aqueous ethanol solution is about 10 to about 50 times the mass of the intermediate product.

* * * * *